United States Patent [19]
Cope et al.

[11] Patent Number: 5,499,975
[45] Date of Patent: *Mar. 19, 1996

[54] SMOOTH TRANSITIONED DILATOR-SHEATH ASSEMBLY AND METHOD

[75] Inventors: Constantin Cope, Elkins Park, Pa.; Patty J. Arnett, Bloomington, Ind.

[73] Assignee: Cook Incorporated, Bloomington, Ind.

[*] Notice: The term of this patent shall not extend beyond the expiration date of Pat. No. 5,011,478.

[21] Appl. No.: 169,508

[22] Filed: Dec. 17, 1993

Related U.S. Application Data

[63] Continuation-in-part of Ser. No. 924,365, Jul. 31, 1992, Pat. No. 5,292,311, which is a continuation of Ser. No. 606,050, Oct. 30, 1990, abandoned, which is a continuation of Ser. No. 304,667, Jan. 31, 1989, Pat. No. 5,011,478.

[51] Int. Cl.$^6$ .......................... A61M 39/00; A61M 5/00
[52] U.S. Cl. .............................. 604/165; 604/264
[58] Field of Search ............................ 604/281, 282, 604/164, 165, 280, 264

[56] References Cited

U.S. PATENT DOCUMENTS

| | | | |
|---|---|---|---|
| 3,459,184 | 8/1969 | Ring | 128/214.4 |
| 3,612,050 | 10/1971 | Sheridan | 128/214.4 |
| 4,502,482 | 3/1985 | DeLuccia | 128/207 |
| 4,772,266 | 9/1988 | Groshong | 604/164 |
| 4,898,591 | 2/1990 | Jang et al. | 604/282 |
| 4,899,787 | 2/1990 | Ouchi et al. | 604/282 |
| 4,961,731 | 10/1990 | Bodicky et al. | 604/281 |
| 5,011,478 | 4/1991 | Cope | 604/165 |
| 5,085,649 | 2/1992 | Flynn | 604/282 |
| 5,215,540 | 6/1993 | Anderhub | 604/281 |
| 5,292,311 | 3/1994 | Cope | 604/165 |
| 5,308,342 | 5/1990 | Sepetka et al. | 604/282 |

*Primary Examiner*—Paul J. Hirsch
*Attorney, Agent, or Firm*—Woodard, Emhardt, Naughton, Moriarty & McNett

[57] ABSTRACT

An introducer set including a sheath and dilator is formed within a heated mold to form a smooth external shape on the set. In one embodiment, the distal end of the sheath is embedded in the dilator and also formed at an angle oblique to the longitudinal axis of the introducer set. In a second embodiment, the distal end of the sheath contacts the dilator at a ledge or lip formed in the dilator, but is not recessed into the dilator at the ledge portion. The outer diameter of the dilator at the transition is formed relatively the same as the distal tip of the sheath so as to provide a smooth transition between the sheath and the dilator. This construction permits the sheath to be inserted into the body with a minimum of trauma to the patient and also permits easy removal of the sheath from the dilator.

16 Claims, 4 Drawing Sheets

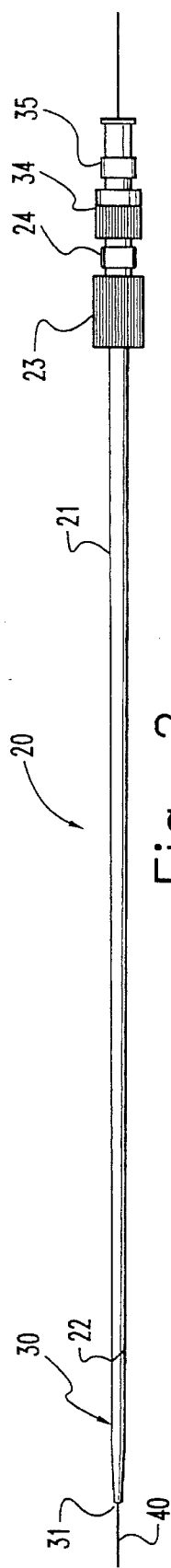
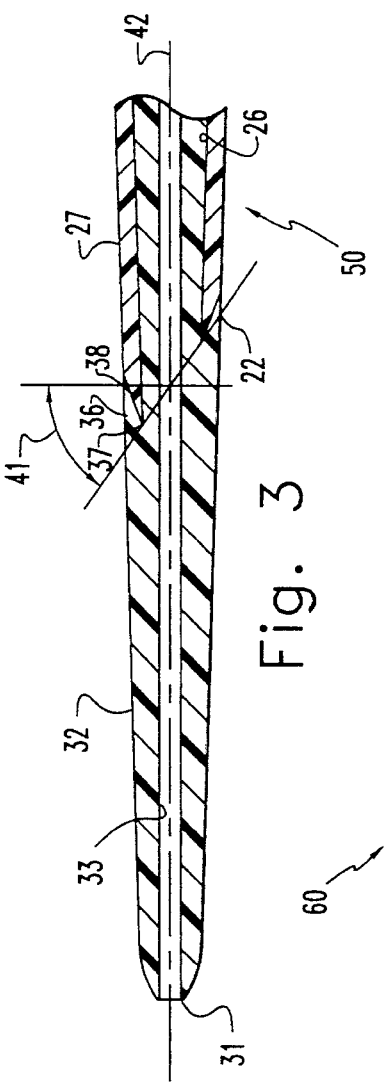
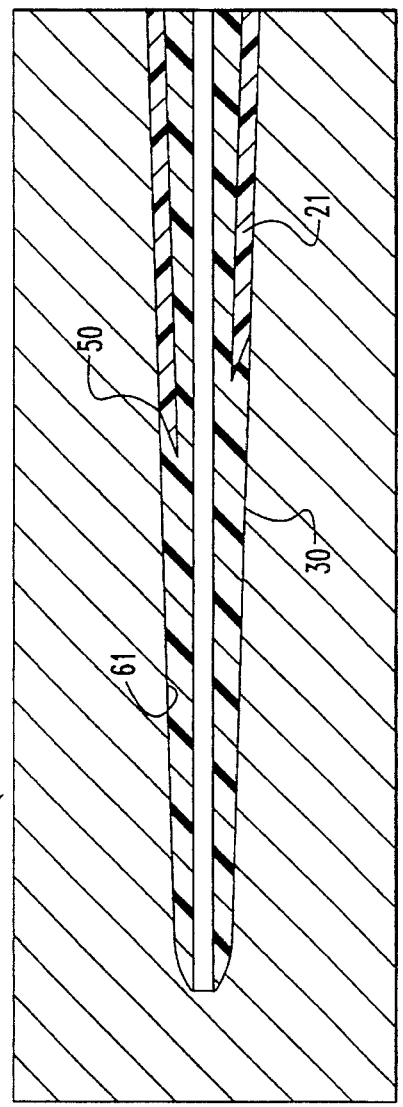
Fig. 2
Fig. 3
Fig. 4

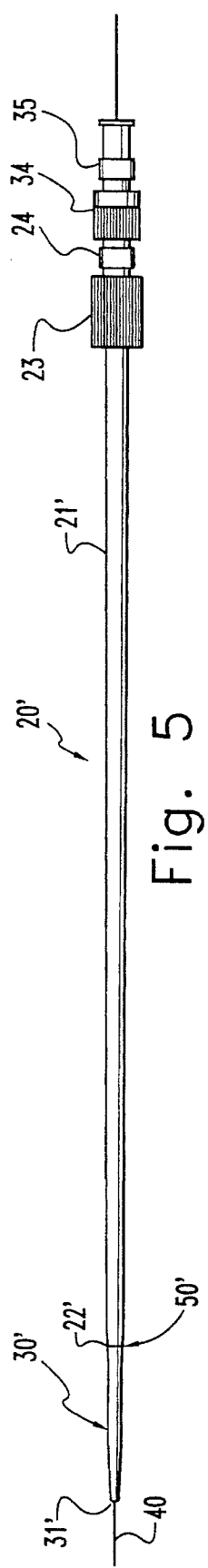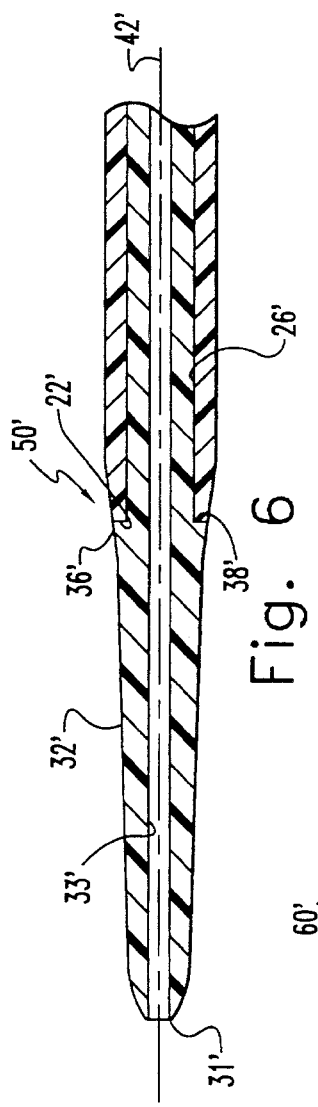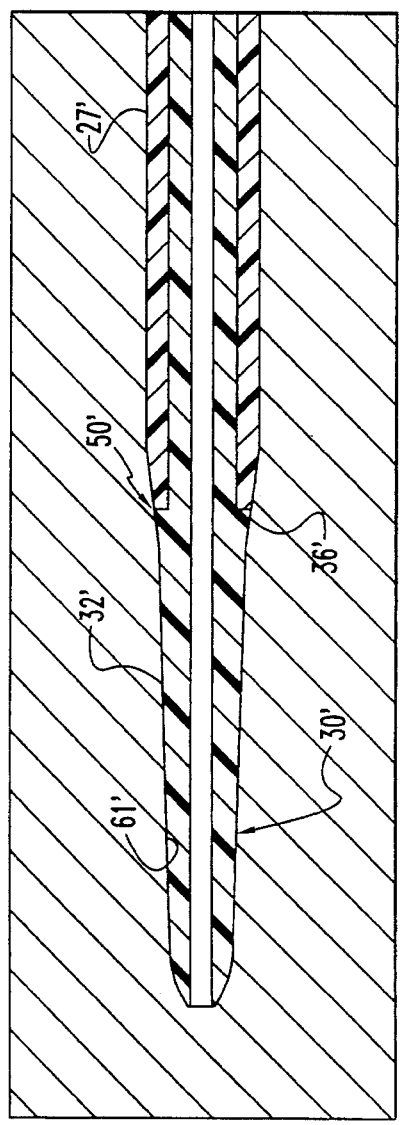

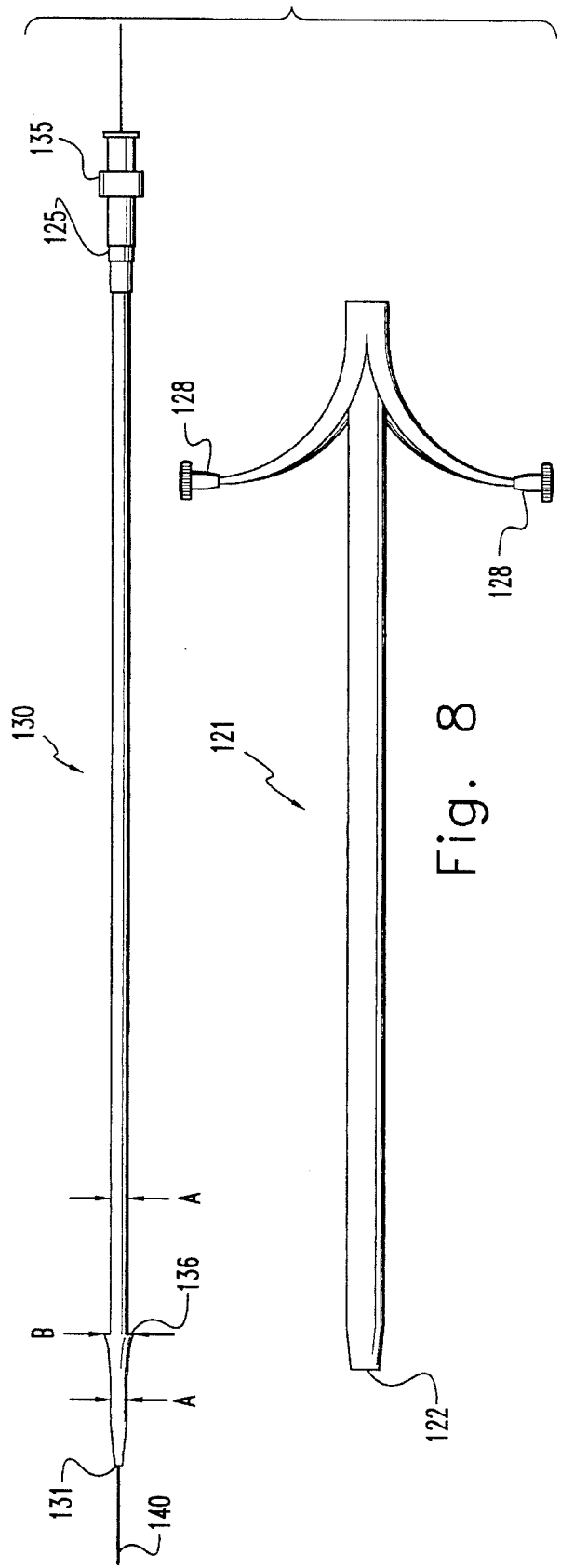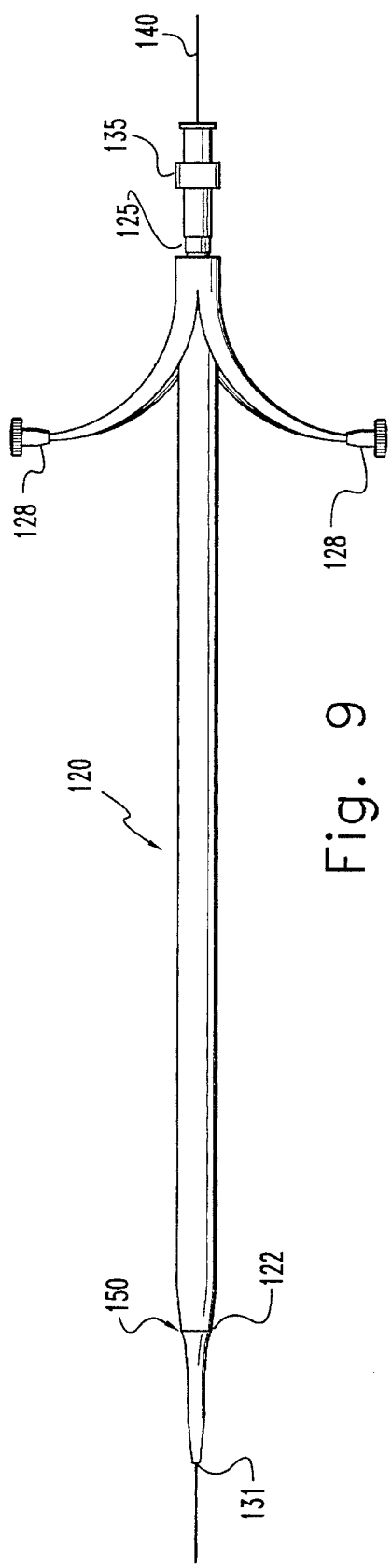
Fig. 8
Fig. 9

1

SMOOTH TRANSITIONED DILATOR-SHEATH ASSEMBLY AND METHOD

REFERENCE TO RELATED APPLICATIONS

This application is a continuation-in-part of U.S. patent application Ser. No. 07/924,365, filed on Jul. 31, 1992, by the same inventive entity, now U.S. Pat. No. 5,292,311 and entitled RECESSED DILATOR-SHEATH ASSEMBLY AND METHOD which is a continuation of U.S. patent application Ser. No. 07/606,050, filed on Oct. 30, 1990, now abandoned, which is a continuation of U.S. patent application Ser. No. 07/304,667, filed on Jan. 31, 1989, now U.S. Pat. No. 5,011,478.

BACKGROUND OF THE INVENTION

1. Field of the Invention

This invention relates generally to a cannula used as an aid for insertion of catheters and other instruments into the body and more particularly to a cannula which abuts a ledge or spur located on or near the distal end of a dilator so as to provide a smooth transition between the sheath and the dilator and to a method for making the dilator-sheath assembly.

2. Brief Description of the Background

It is a frequent practice when introducing balloon, electrode, closed end, and other catheters or instruments into the body, to first introduce a cannula or sheath to aid in the introduction of the catheter or other instruments. Frequently the cannula or sheath will be placed on a dilator which is used on a wire guide to dilate a puncture made by a needle. It is desirable when inserting the dilator that the dilator's outside surface be as smooth as possible in order to prevent patient discomfort. To make insertion of the cannula or sheath as atraumatic as possible, it is also important that the transitions between the dilator and the cannula or sheath be as even as possible.

The current design of introducer systems includes a dilator, or dummy catheter, which is surrounded by the sheath. The sheath is frequently made of thin walled Teflon, although other materials may be used. Typically, the distal end of the sheath is tapered and fitted to the dilator. However, the fit of the sheath onto the dilator does not always create a transition which is smooth enough so that the dilator and sheath will pass easily through the tissue. Therefore, whenever fibrous tissue is encountered during the introduction of the sheath dilator combination, some resistance is encountered when the transition between the dilator and sheath is advanced through the tissue. In some cases, the distal end of the sheath is damaged during advancement through fibrous tissue. As advancement continues, the deformed sheath tip becomes harder to advance because of tearing and flaring, damaging the tissue and creating more trauma to the patient.

The present invention provides a dilator to sheath transition which is smooth, thus preventing undue trauma upon insertion into the patient.

SUMMARY OF THE INVENTION

One embodiment of the dilator-sheath assembly of the present invention is a cannula with its distal tip recessed into a dilator to prevent trauma upon insertion in patients. Because the transition between the dilator and the cannula is smooth due to the recess, little resistance is encountered when inserting the cannula. Moreover, if the recessed distal end is formed at an angle oblique to the axis of the cannula, the cannula may be easily freed from the dilator by twisting the cannula about the dilator.

A second embodiment of the present invention is to provide a dilator-sheath assembly wherein the distal tip of the sheath is not recessed into the dilator, but rather, the distal tip contacts a ledge or lip located at the distal end of the dilator. At the point of contact, the ledge and the sheath have relatively the same outer diameter so as to provide a smooth transition between the cannula and the dilator, to prevent trauma upon insertion in patients. Because the transition between the dilator and the cannula is smooth, due to the relatively similar outer diameters, little resistance is encountered when inserting the cannula. Additionally, the cannula may be easily freed from the dilator by twisting the cannula about the dilator.

One embodiment of the method of making the dilator-sheath assembly of the present invention might include heating a mold to a temperature sufficient to form a dilator-sheath assembly and forcing the dilator-sheath assembly against the mold to form it.

It is an object of the present invention to provide an improved dilator-sheath assembly which causes little trauma upon insertion into the body.

It is another object to provide a dilator-sheath assembly wherein the dilator is easily removed from the sheath.

It is a further object to provide a method for making the dilator-sheath assembly described above.

Further objects and advantages will become apparent from the following description.

BRIEF DESCRIPTION OF THE DRAWINGS

FIG. 2 is a side view of the dilator-sheath assembly of a first preferred embodiment of the present invention.

FIG. 3 is a an enlarged fragmentary cross-sectional view of the structure of FIG. 2.

FIG. 4 is a cross-sectional view of a mold appropriate for use in forming the dilator-sheath assembly of FIG. 2 and showing a dilator-sheath assembly inserted in the mold.

FIG. 5 is a side view of the dilator-sheath assembly of a preferred embodiment of the present invention.

FIG. 6 is a an enlarged fragmentary cross-sectional view of the structure of FIG. 5.

FIG. 7 is a cross-sectional view of a mold appropriate for use in forming the dilator-sheath assembly of FIG. 5 and showing a dilator-sheath assembly inserted in the mold.

FIG. 8 is a side view of the dilator and sheath of the dilator-sheath assembly used in an alternate embodiment of the present invention.

FIG. 9 is a side view of the dilator-sheath assembly of an alternate embodiment of the present invention.

DESCRIPTION OF THE PREFERRED EMBODIMENT

Figure 1:
FIG. 1 is a side view of a catheter introducer made in accordance with the prior art.

For the purposes of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates. Further, like reference numerals denote like parts throughout the drawings.

A prior art catheter introducer set is shown in FIG. 1. The structure is commercially available, one example being a Desilets-Hoffman introducer set available from Cook Incorporated of Bloomington, Ind. under the designation TSSN or VSSN. One important feature of such a structure is the interlocking feature of the sheath and dilator which is provided by the Luer lock connection of the sheath and dilator. The interlocking feature ensures that the sheath and dilator are fixed relative to one another during insertion. The prior art dilator-sheath transition assembly shown in FIG. 1 does not have a smooth transition between the sheath and the dilator. Rather, the distal end of the sheath in the prior art assembly is exposed to tissue during insertion.

Referring now to the recessed dilator-sheath assembly shown in FIG. 2, there is illustrated a dilator-sheath assembly 20 formed according to a first preferred embodiment of the present invention. A cannula or sheath 21 is disposed coaxially about the dilator 30, which is in turn disposed coaxially about a wire guide 40. A portion of the dilator 30 extends distally beyond the distal end 22 of the sheath 21. The dilator's distal end 31 is tapered for enlarging the puncture site to accommodate the sheath. At the transition 22, the dilator's external diameter changes so that proximal to the transition 22, the dilator's external diameter is smaller than the external diameter distal to transition 22. With the exceptions noted, the dilator 30 is tubular and of approximately uniform internal and external diameter, having smooth external and internal surfaces, 32 and 33 respectively. The sheath 21 is also of approximately uniform thickness and diameter except at its distal end 22 where there is an external taper. The sheath is also snug about the dilator 30. At its proximal end, the sheath 21 is terminated in a cap 23 having a male Luer lock connector 24. Proximally, the dilator 30 terminates in a cap 34. The cap 34 includes a female Luer lock connector which accepts the male Luer lock connector 24. The proximal termination of cap 34 is a male Luer lock connector 35. The connecting of the male Luer lock connector 35 and the female Luer lock of the cap 34 interlocks the sheath 21 and dilator 30.

FIG. 3 is an enlarged fragmentary cross-section taken along the longitudinal axis of the dilator-sheath assembly 20 and showing the distal end of the assembly 20 in detail. The wire guide 40 is shown removed. The dilator 30 is shown extending distally of the distal end 22 of the sheath 21. In general, the dilator 30 extends distally of the sheath for about 2 cm., more or less. Such extension is required to provide enough distance between the distal end 31 of the dilator 30 and the transition 50 to the sheath 21 so that a smooth taper is gradually made from the distal end 31 of the dilator 30 to the transition 50.

Throughout the length of the tubular sheath 21 it is disposed coaxially with the tubular dilator 30. Such length is approximately 16 cm, more or less, as the application requires. The inner diameter of the sheath 21 is such that its inner surface 26 is closely against the outer surface 32 of the dilator 30 without being so tight as to prevent movement of the sheath on the dilator. Thus, in one specific embodiment of the invention for a major portion of the length of the sheath 21 the I.D. is 0.095"±0.001" and the O.D. of the dilator 30 is 0.092"±0.002". The outer diameter of the dilator 30 increases near the tip 22 of the sheath, cutting back toward the distal end to create a spur or overlap 36 under which the distal end 22 of the sheath 21 is received. In other words, spur 36 can be thought of as creating an annular abutment surface against which the distal end 22 of the sheath abuts to thereby shield the end of the sheath when the assembly is inserted into the body. As a result of this recess 37 and the distal end 22 of the sheath 21 being received therein, a smooth transition 50 from the dilator 30 to the sheath 21 is created which eases patient stress upon insertion. Moreover, the external surface 32 of the dilator is completely even with the external surface 27 of the sheath so that the transition provides a continuous surface from external surface 32 to external surface 27. There are no edges exposed to catch on fibrous tissue.

The tip 22 of the sheath 21 as well as the recess 37 are formed at an angle 41 which is oblique to the longitudinal axis 42 of the dilator-sheath assembly 20. The most proximal edge 38 of the spur 36 is also formed at an angle oblique to the longitudinal axis. These oblique angles of the spur 36 and the distal sheath tip 22 are arranged in such a way that the embedded end 22 of the sheath 21 and the recess 37 form two coinciding ellipses. The tubular structure 21 can be easily freed from the dilator 30 by first rotating the dilator 30 relative to the sheath about the axis 42 and then withdrawing the dilator 30 from the sheath.

The recessed dilator-sheath assembly of the present invention may be used in conjunction with various currently available catheter introducer sets designs. For example, as shown in FIGS. 2-4 and described above, a catheter introducer set, including a sheath that is not removable or splittable, like the above mentioned Desilets-Hoffman introducer set of FIG. 1, may be formed with the recessed dilator sheath of the present invention. Alternatively, the recessed dilator sheath of the present invention may be used in a catheter introducer set having a sheath which is removable or splittable. In this alternate embodiment of the present invention, the recessed dilator sheath is used with a sheath as described, for example, in U.S. Pat. No. Re. 31,855.

The recessed dilator-sheath assembly of the present invention may be used as follows. First, a percutaneous needle is inserted through the skin and body tissue into the vein or artery or other vessel to be catheterized. A wire guide 40 may then be inserted into the body and vessel through the needle. The needle is then removed from the puncture site, leaving the wire guide 40 in place. The dilator-sheath assembly 20 is then inserted into the body over the wire guide 40. As the dilator 30 is advanced into the body, the puncture hole gradually increases in diameter as a result of the distal tapering of the dilator 30. The insertion proceeds smoothly past the transition 50 between the dilator 30 and sheath 21 because the sheath's distal end 22 is embedded in the dilator 30 and cannot catch on body tissue. Twisting the dilator relative to the sheath about the axis 42 frees the sheath 21 from the recess 37, thus facilitating the removal of the dilator 30 from the body and the sheath. The sheath 21 remains in the the body allowing access to the target body cavity.

Teflon (Teflon is the Dupont trademark for polytetrafluoroethylene) used in the preferred embodiments as the sheath material is virgin material, i.e., has not previously been used or reground. It is free of foreign matter and dye marks. These characteristics are required to ensure compatibility for insertion into the body.

A mold 60 as shown in FIG. 4 may be used to form the distal end of dilator-sheath assembly 20. In order to make the dilator-sheath assembly, the mold 60 is heated to a temperature at which the dilator material softens and becomes flowable. The dilator-sheath assembly 20 is inserted into the mold 60. The internal surface 61 of the mold 60 defines a space identical to the external surface of the dilator-sheath assembly 20 described by the line from surface 32 to surface 27. The recess defined by the mold's internal surface 61 is such that the dilator-sheath assembly 20 is insertable far enough within the mold 60 so that the dilator-sheath transition 50 is well within the mold 60. Because of this resultant flowability of the dilator material, the spurs 36 on the dilator form immediately next to the tapered distal end 22 of the sheath 21. The sheath 21, made of a higher melting material, typically Teflon, than the dilator 30, will not become flowable. However, it is important in this process that the mold 60 not be heated to a temperature sufficient to cause the sheath material to become softened and flowable. This is because the sheath material must remain rigid in order to partially define the boundaries to which the dilator material is free to flow. Thus, the internal surface 61 of the mold 60 defines the latitudinal boundaries while the distal end 22 of the sheath 21 defines the longitudinal boundaries of flow. As a result of the heating the dilator external surface 32 and the sheath external surface 27 are coplaner immediately proximal to the distal taper of the dilator 30. Once the desired result is achieved, i.e. the dilator material flows to form the recess 37 defined by the distal end 22 of the sheath 21, the mold and dilator-sheath assembly therein are allowed to cool, thus firmly setting the dilator material. The dilator-sheath assembly may then be removed from the mold.

Referring now to FIGS. 5 and 6, there is illustrated a second preferred embodiment of a smooth transitioned dilator-sheath assembly 20' formed according to the present invention, wherein the sheath is not recessed into the dilator. As with the recessed dilator-sheath assembly described above, a cannula or sheath 21' is disposed coaxially about the dilator 30', which is in turn disposed coaxially about a wire guide 40'. A portion of the dilator 30' extends distally beyond the distal end 22' of the sheath 21'. The dilator's distal end 31' is externally tapered for enlarging the puncture site to accommodate the sheath. With the exception of an annular lip or ledge 36' located at transition 50', the outer diameter of the dilator is the same both inside and outside the sheath, from the proximal end of the dilator 30' up to the beginning of the external taper at the distal end 31' of the dilator. With the exceptions noted, the dilator 30' is tubular and of approximately uniform internal and external diameter, having smooth external and internal surfaces, 32's and 33' respectively. The sheath 21' is also of approximately uniform thickness and diameter except at its distal end 22' where there is an external taper, which results in the distal end 22' of the sheath 21' comprising thinner material than the proximal end of the sheath 21'. The sheath 21' fits snugly about the dilator 30'. At it's proximal end, the sheath 21' is terminated in a cap 23 having a male Luer lock connector 24. Proximally, the dilator 30's terminates in a cap 34. As described above, the cap 34 includes a female Luer lock connector which accepts the male Luer lock connector 24. The proximal termination of cap 34 is a male Luer lock connector 35. The connecting of the male Luer lock connector 35 and the female Luer lock of the cap 34 interlocks the sheath 21 and dilator 30 against movement relative to each other.

FIG. 6 is an enlarged fragmentary cross-section taken along the longitudinal axis of the dilator-sheath assembly 20' and showing the distal end of the assembly 20' in detail. The wire guide 40 is shown removed. The dilator 30' is shown extending distally of the distal end 22' of the sheath 21'. As noted above, with the exception of the annular ledge 36', which starts at the transition 50' and then tapers into the body of the dilator, the dilator has the same outer diameter inside the sheath as it does outside the sheath, from the proximal end of the dilator 30' to the beginning of the external taper at the distal end 31' of the dilator. In general, the dilator 30' extends distally of the sheath for about 2 cm., more or less.

Throughout the length of the tubular sheath 21' it is disposed coaxially with the tubular dilator 30'. Such length is approximately 16 cm, more or less, as the application requires. The inner diameter of the sheath 21' is such that its inner surface 26' fits closely against the outer surface 32' of the dilator 30' without being so tight as to prevent movement of the sheath on the dilator. Thus, in one specific embodiment of the invention for a major portion of the length of the sheath 21 the I.D. is 0.095"±0.001" and the O.D. of the dilator 30 is 0.092"±0.002". At the transition 50', the outer diameter of the dilator 30' is increased slightly to form a small annular ledge or lip 36' against which the distal end 22' of the sheath 21' is in contact. Annular lip 36' includes a face or surface 38' which is perpendicular to the axis 42' of the body of the dilator 30'. The distal end 22' of the sheath 21' abuts the face 38' of the annular ledge 36' so as to shield the end of the sheath when the assembly is inserted into the body.

Additionally, both the distal tip 22' of the sheath 21' and the annular ledge 36' have relatively the same outer diameter at the transition 50', which permits the distal end 22' of the sheath 21' to contact the annular ledge 36' to form a smooth transition 50' from the dilator 30' to the sheath 21'. This smooth transition 50' eases patient stress upon insertion. Moreover, the external surface 32' of the dilator is completely flush or even with the external surface 27' of the sheath so that the transition provides a continuous surface from external surface 32' to external surface 27'. There are no edges exposed to catch on fibrous tissue. Further, the outer diameter of the annular ledge 36' tapers from the transition 50', towards the distal end 31' of the dilator 30', until the outer diameter of the dilator 30' is once again the same as is present inside the sheath 21'.

The distal end 22' of the sheath 21' of the present embodiment includes a surface which is perpendicular to the axis 42' of the body of the dilator-sheath assembly 20'. The perpendicular surface at the distal end of the sheath 21' abuts and is flush with the perpendicular surface formed on the face of annular ledge 36'. In the present embodiment, the sheath 21' is not recessed into the dilator 30'.

Further, as can be seen in FIGS. 2–4, the distal end of the sheath 21' is tapered such that the outer diameter of the distal tip of the sheath 21' is thinner at the distal end 22' than at the proximal end of the sheath 21'. For example, in one embodiment the thickness of the sheath at it's proximal end and along a major portion of the body of the sheath is 0.010 in. The thickness of the sheath at the transition 50' is 0.005 in. As such, the tubular structure 21' can be easily freed from the dilator 30' by first rotating the dilator 30' relative to the sheath about the axis 42', to loosen the sheath from the dilator, and then withdrawing the dilator 30' from the sheath. The distal end 22' of the sheath 21' is sufficiently thin so that it can easily deform outwardly when the dilator 30' is withdrawn through it. Further, the annular ledge 36' is designed to be sufficiently small so that it need not greatly deform the sheath 21' outwardly to pass through it. As the majority of the dilator outside the sheath is of the same or smaller outer diameter as the dilator inside the sheath, with the exception of the outward flexing of the sheath at the transition, there is no need for the sheath to stretch greatly when the dilator is removed therefrom.

The non-recessed smooth transitioned dilator-sheath assembly 21' of the present embodiment may be used in conjunction with various currently available catheter introducer sets designs. For example, as shown in FIGS. 5–7 and described above, a catheter introducer set, including a sheath that is not removable or splittable, like the above mentioned Desilets-Hoffman introducer set of FIG. 1, may be formed with the smooth transitioned dilator sheath of the present invention. Alternatively, the smooth transitioned dilator-sheath assembly 20' of the present invention may be used in a catheter introducer set having a sheath which is removable or splittable. In this alternate embodiment of the present invention, the smooth transitioned dilator sheath is used with a sheath as described, for example, in U.S. Pat. No. Re. 31,855.

Further, the non-recessed smooth transitioned dilator sheath of the present invention may be used as follows. First, a percutaneous needle is inserted through the skin and body tissue into the vein or artery or other vessel to be catheterized. A wire guide 40' may then be inserted into the body and vessel through the needle. The needle is then removed from the puncture site, leaving the wire guide 40' in place. The smooth transitioned dilator-sheath assembly 20' is then inserted into the body over the wire guide 40'. As the dilator 30' is advanced into the body, the puncture hole gradually increases in diameter as a result of the distal tapering of the dilator 30'. The insertion proceeds smoothly past the transition 50' between the dilator 30' and sheath 21' because the sheath's distal end 22' abuts the annular ledge 36' of the dilator 30' and cannot catch on body tissue. Twisting the dilator 30' relative to the sheath 21' about the axis 42' frees the sheath 21' from contact with the annular lip 36', thus facilitating the removal of the dilator 30' from the body and the sheath 21'. The sheath 21' remains in the the body allowing access to the target body cavity.

As with the above described recessed dilator-sheath assembly embodiment, Teflon (Teflon is the Dupont trademark for polytetrafluoroethylene) used in the preferred embodiments as the sheath material is virgin material, i.e., has not previously been used or reground. It is free of foreign matter and dye marks. These characteristics are required to ensure compatibility for insertion into the body.

The smooth transitioned dilator-sheath assembly of the present non-recessed embodiment may be formed similarly to that described in connection with FIG. 4, above. A mold 60', as shown in FIG. 7, may be used to form the distal end of dilator-sheath assembly 20'. In order to make the dilator-sheath assembly, the mold 60' is heated to a temperature at which the dilator material softens and becomes flowable. The dilator-sheath assembly 20' is inserted into the mold 60'. The internal surface 61 of the mold 60' defines a space identical to the external surface of the dilator-sheath assembly 20' described by the line from surface 32' to surface 27'. The recess defined by the mold's internal surface 61' is such that the dilator-sheath assembly 20' is insertable far enough within the mold 60' so that the dilator-sheath transition 50' is well within the mold 60'. Because of this resultant flowability of the dilator material, the annular ledge 36' on the dilator forms immediately adjacent to the tapered distal end 22' of the sheath 21'. The sheath 21', made of a higher melting material, typically Teflon, than the dilator 30', will not become flowable. However, it is important in this process that the mold 60' not be heated to a temperature sufficient to cause the sheath material to become softened and flowable. This is because the sheath material must remain rigid in order to partially define the boundaries to which the dilator material is free to flow. Thus, the internal surface 61' of the mold 60' defines the latitudinal boundaries while the distal end 22' of the sheath 21' defines the longitudinal boundaries of flow. As a result of the heating the dilators external surface 32' and the sheaths external surface 27' are coplaner at the transition 50'. Once the desired result is achieved, i.e. the dilator material flows to form an annular ledge 36' having a face 38' which contacts the distal end 22' of the sheath 21', the mold and dilator-sheath assembly therein are allowed to cool, thus firmly setting the dilator material. The dilator-sheath assembly may then be removed from the mold.

An alternate embodiment to that shown in FIG. 5 will now be described in connection with FIGS. 8 and 9. Referring now to FIG. 9, there is shown a smooth transitioned dilator-sheath assembly 120 in accordance with the present invention. FIG. 8 shows the dilator 130 and the sheath 121 of the dilator-sheath assembly 120 of the present embodiment with the sheath removed from the dilator. The smooth transitioned dilator-sheath assembly 120 is virtually identical in manufacture and use as the dilator-sheath assembly 20 of FIGS. 5–7, with two primary exceptions. First, rather than using a mating luer lock connector assembly, the dilator-sheath assembly incorporates a single male luer lock connector 135 and a spacer 125. The luer lock connector 135 is located at the proximal end of the dilator 130, as shown in FIG. 8. The spacer 125 fits coaxially about the dilator 130, adjacent to the luer lock connector 135. The outer diameter of the spacer 125 is designed to be greater than the inner diameter of the sheath 121 so that when the sheath 121 is slid over the dilator, the sheath 121 cannot travel over the spacer 125 when a force is applied to the distal end 122 of the sheath 121. The reason for this design is to keep the sheath 121 in a known position when forming the annular ledge 136 at the distal end 131 of the dilator 130 in the manner described herein in connection with FIG. 7.

In the present embodiment, the outer diameter A of the dilator inside the sheath, and again after the transition point 150 is 0.105 in. At the transition 150, the outer diameter B of the annular ledge 136 is 0.109 in. As described above in connection with the previous embodiment, the outer diameter of the dilator is tapered from the transition 150 until the outer diameter of the dilator 130 again returns to 0.105 in. The taper from the transition 150 until the outer diameter returns to 0.105 in is a distance of 2 mm. The outer diameter of the dilator 130 again tapers at it's distal end 131, as described in connection with the above embodiments.

Additionally, the embodiment of the present invention is shown in FIGS. 8 and 9 as incorporating a splittable sheath 121 of the type described in U.S. Pat. No. 4,581,025 to Timmermans, that patent incorporated herein by reference. Other types of splittable sheaths, such as shown in U.S. Pat. No. 4,306,562 to Osborne, that patent additionally incorporated herein by reference, and non-splittable sheaths may be used with all embodiments of the present invention. By using the sheath 121 shown in FIGS. 5 and 6 in connection with the present invention, it is possible, if necessary, to remove the sheath without removing objects located through the sheath. Pulling apart the tabs 128 allows the sheath 121 to be torn londitudinally along its length. Additionally, the presently disclosed design of sheath 121 has the added advantage of permitting the user to temporarily block blood flow or air aspiration during use when no dilators or catheters are located in the sheath lumen, as described in the U.S. Pat. No. 4,581,025.

While particular embodiments of the invention have been illustrated and described in detail in the drawing and foregoing description, it is to be understood that this description is made only by way of example and not as a limitation to the scope of the invention which is claimed below.

We claim:

1. A dilator-sheath assembly for use in percutaneous entry comprising:

a sheath having an external surface and one end adapted to be inserted into the body;

a dilator within said sheath and having an external surface and a distal portion extending beyond the one end of the sheath so as to define a transition, said dilator having two ends and a longitudinal passageway extending between said ends, said external surface being formed to include an annular abutment surface against which said one end of said sheath abuts such that said transition from said external surface of said dilator to said external surface of said sheath is smooth, whereby said dilator shields said one end of said sheath when the dilator-sheath assembly is inserted in the body;

wherein said dilator is composed of a material having a lower melting point than said sheath.

2. The dilator-sheath assembly of claim 1 wherein said annular abutment surface includes a face located perpendicular to an axis through the body of said dilator and extending at right angles from the body of said dilator and wherein said face contacts said one end of said sheath.

3. The dilator-sheath assembly of claim 1 wherein the outer diameter of said dilator within said sheath is the same as or greater than the outer diameter of said dilator extending beyond said sheath distal from said transition.

4. The dilator-sheath assembly of claim 2 wherein said dilator is removable from the body and sheath by withdrawing the dilator through the sheath, said one end of said sheath being sufficiently thin to allow said one end to flex outwardly to allow for such withdrawal.

5. The dilator-sheath assembly of claim 2 wherein said sheath is externally tapered proximal to said one end of said sheath.

6. The dilator-sheath assembly of claim 2 wherein said sheath and dilator have longitudinal axes and are coaxial, said one end of said sheath being formed at an angle perpendicular to the longitudinal axis of said sheath and said dilator.

7. The dilator-sheath assembly of claim 2 wherein the outer diameter of said dilator proximal to said annular abutment is the same as the outer diameter of said dilator distal to said annular abutment.

8. A dilator-sheath assembly for use in percutaneous entry comprising:

a sheath formed of flexible plastic material, said sheath being compatible for insertion within the body and having one end adapted to be inserted in the body;

a dilator within said sheath, said dilator defining a longitudinal bore sized to receive a guide wire therethrough and having a distal end extending beyond said one end of said sheath, and said dilator formed of flexible plastic material, said dilator being composed of a material having a lower melting point than said sheath; and a transition defined by an increase in the outer diameter of said dilator such that the outer diameter of said dilator is approximately equal to the outer diameter of said sheath at said one end of said sheath; and wherein said transition includes an annular abutment surface formed on said dilator against which said one end of said sheath abuts such that said transition is smooth.

9. The dilator-sheath assembly of claim 8 wherein the outer diameter of said dilator within said sheath proximal to said transition is the same as or greater than the outer diameter of said dilator extending beyond said sheath distal said transition.

10. The dilator-sheath assembly of claim 8 wherein said annular abutment surface includes a face located perpendicular to the longitudinal axis of said dilator and extends perpendicularly from the body of said dilator at said transition so that said one end of said sheath abuts said face at said transition.

11. The dilator-sheath assembly of claim 10 wherein said sheath is externally tapered proximal to said one end of said sheath.

12. A method of making a dilator-sheath assembly comprising the steps of:

placing a sheath upon a dilator to form a dilator-sheath assembly with the sheath surrounding the dilator;

heating said dilator-sheath assembly within a mold to a temperature sufficient to cause the dilator material to become flowable but insufficient to cause the sheath material to become flowable; and allowing said dilator material to flow to form an annular abutment surface which abuts one end of said sheath, said annular abutment surface including a face connected to and extending perpendicularly from the body of said dilator, while forcing the outer surface of said dilator-sheath assembly against a surface of said mold to form a smooth transition between the outer surface of the dilator and the outer surface of the sheath.

13. A method of making a dilator-sheath assembly comprising the steps of:

placing a sheath upon a dilator to form a dilator-sheath assembly with the sheath surrounding the dilator;

heating a mold to a temperature sufficiently hot to form the dilator under pressure; and forcing the dilator-sheath assembly against the mold to form an annular ledge in the dilator against the end of said sheath such that a smooth transition between the outer surface of the dilator and the outer surface of the sheath is formed, and such that said sheath does not extend into said ledge.

14. The method of claim 13 additionally comprising the step of allowing the mold and dilator-sheath assembly to cool until the dilator-sheath assembly is sufficiently rigid to retain its shape.

15. The method of claim 14 where the mold has a smooth internal mold surface and wherein the forcing is accomplished by inserting the dilator-sheath assembly into the mold.

16. A dilator-sheath assembly comprising:

a sheath having one end adapted to be inserted into the body, said sheath being splittable along it's length;

a dilator within said sheath and having a distal end extending beyond the one end of the sheath, said dilator including an annular ledge near said distal end, said annular ledge including a face located perpendicular to the longitudinal axis of said dilator wherein said end of said sheath abuts said face, whereby said ledge shields said one end of said sheath when the dilator-sheath assembly is inserted in the body, and whereby said outer diameter of said dilator at said ledge tapers away from said ledge until said outer diameter of said dilator distal from said ledge is equal to or less than the outer diameter of the dilator located within said sheath;

said dilator and sheath being heat formed as an assembly causing the sheath and dilator to have an exact fit wherein said face is flush with said end, and having a smooth outer surface transition between said dilator and said sheath.

* * * * *

UNITED STATES PATENT AND TRADEMARK OFFICE
CERTIFICATE OF CORRECTION

PATENT NO. : 5,499,975
DATED : March 19, 1996
INVENTOR(S) : Constantin Cope et al.

It is certified that error appears in the above-indentified patent and that said Letters Patent is hereby corrected as shown below:

In col. 1, line 38, change "transitions" to --transition--.
In col. 1, line 47, "Therefore" should begin a new paragraph.
In col. 5, line 47, change "32's" to --32'--
In col. 5, line 55, change "30's" to --30'--
In col. 7, line 34, delete "the", third occurrence.
In col. 10, line 1, insert --to-- after "distal"

Signed and Sealed this

Twenty-seventh Day of January, 1998

Attest:

BRUCE LEHMAN

Attesting Officer

Commissioner of Patents and Trademarks